United States Patent

Maeda et al.

[11] Patent Number: 5,948,803
[45] Date of Patent: Sep. 7, 1999

[54] N-SUBSTITUTED DIOXOTHIAZOLIDYLBENZAMIDE DERIVATIVES AND PROCESS FOR PRODUCING THE SAME

[75] Inventors: Toshio Maeda, Tokyo; Masahiro Nomura; Katsuya Awano, both of Tochigi; Susumu Kinoshita, Saitama; Hiroya Satoh, Tochigi; Koji Murakami, Tochigi; Masaki Tsunoda, Tochigi, all of Japan

[73] Assignee: Kyorin Pharmaceutical Co., Ltd., Tokyo, Japan

[21] Appl. No.: 09/077,899
[22] PCT Filed: Dec. 16, 1996
[86] PCT No.: PCT/JP96/03664
   § 371 Date: Jun. 16, 1998
   § 102(e) Date: Jun. 16, 1998
[87] PCT Pub. No.: WO97/22600
   PCT Pub. Date: Jun. 26, 1997

[30] Foreign Application Priority Data

Dec. 18, 1995 [JP] Japan .................................. 7-348341

[51] Int. Cl.[6] ........................ A61K 31/425; C07D 277/34
[52] U.S. Cl. ............................................. 514/369; 548/183
[58] Field of Search ............................... 548/183; 514/369

[56] References Cited

U.S. PATENT DOCUMENTS 5,308,856  5/1994  Ohnota et al. .
5,342,850  8/1994  Ohnota et al. .

Primary Examiner—Patricia L. Morris
Attorney, Agent, or Firm—Oblon, Spivak, McClelland, Maier & Neustadt, P.C.

[57] ABSTRACT

The invention provides novel N-substituted dioxothiazolidylbenzamide derivatives that improve the insulin resistance and have potent hypoglycemic effect and lipid-lowering effect, and the process for preparing them, and relates to N-substituted dioxothiazolidylbenzamide derivatives characterized by being represented by a general formula (1)

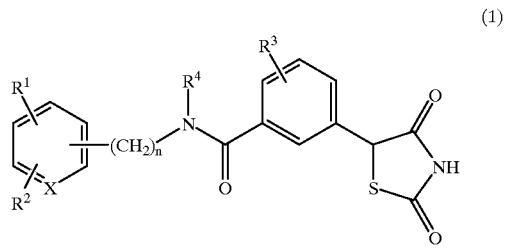

[wherein $R^1$ and $R^2$ denote identically or differently hydrogen atoms, lower alkyl groups with carbon atoms of 1 to 4, lower alkoxy groups with carbon atoms of 1 to 3, lower haloalkyl groups with carbon atoms of 1 to 3, lower haloalkoxy groups with carbon atoms of 1 to 3, halogen atoms or hydroxyl groups, or $R^1$ and $R^2$ combine to form a methylenedioxy group, $R^3$ denotes a hydrogen atom, lower alkoxys group with carbon atoms of 1 to 3, hydroxyl group or halogen atom, $R^4$ denotes a hydrogen or lower alkyl group with carbon atoms of 1 to 3, n denotes an integer of 0 to 2, and X denotes N or CH], and process for preparing the same.

12 Claims, No Drawings

N-SUBSTITUTED DIOXOTHIAZOLIDYLBENZAMIDE DERIVATIVES AND PROCESS FOR PRODUCING THE SAME

TITLE OF THE INVENTION

N-substituted dioxothiazolidylbenzamide derivatives and the process for preparing the same

TECHNICAL FIELD

The present invention relates to novel N-substituted dioxothiazolidylbenzamide derivatives that improve the diabetes mellitus and hyperlipidemia, and the process for preparing the same.

BACKGROUND TECHNOLOGIES

So far, as oral therapeutic drugs for diabetes mellitus, biguanide type and sulfonylurea type compounds have been used. However, with biguanide type compounds, lactic acidosis or hypoglycemia is caused and, with sulfonylurea type compounds, serious and prolonged hypoglycemia is caused, and the adverse effect thereof is posing a problem. Therefore, the appearance of new therapeutic agent without such defect is desired.

Moreover, it is known that some of the 2,4-dioxothiazolidine derivatives exhibit hypoglycemic and lipid-lowering effects (*Journal of Medicinal Chemistry*, vol. 35, P. 1853 (1992) and Japanese Unexamined Patent Publication No. Hei 1-272573), but, in all of these compounds, the position of substitution on middle benzene ring that connects with 2,4-dioxothiazolidine ring and aromatic ring is p-position; the former has oxazole ring for the aromatic ring and the latter has sulfonylamide for the linkage. In addition, both have a carbon chain between middle benzene ring and thiazolidine-2,4-dione ring, structurally different from N-substituted dioxothiazolidylbenzamide derivatives of the present invention.

On the other hand, it has been clear that aldose reductase takes part in the crisis of diabetic complication (*Journal of American Medical Association*, vol. 246, p. 257 (1981)).

Moreover, it is known that some of the 2,4-dioxothiazolidines exhibit aldose reductase inhibitory activity (*Chemical and Pharmaceutical Bulletin*, vol. 30, p. 3601 (1982) and Japanese Unexamined Patent Publication No. Hei 5-92960). In the former, the 2,4-dioxothiazolidine ring and the carboxyl group are p-substituted via middle benzene ring and in the latter, the bonding mode to middle benzene ring is acylamino, and the like. Therefore they are sturcturally different from N-substituted dioxothiazolidylbenzamide derivatives of the present invention, and additionally they have only weak hypoglycemic effect.

For the non-insulin dependent diabetes mellitus (NIDDM) that accounts for the majority of diabetic patients, an effective blood sugar-lowering drug with high safety that allows to prevent or cure the complications together with ability for improving insulin resistance and lowering blood sugar is desired.

DISCLOSURE OF THE INVENTION

As a result of diligent studies on a drug with high safety that improves the insulin resistance and has more potent hypoglycemic effect, the inventors have found that novel N-substituted dioxothiazolidylbenzamide derivatives represented by a following general formula (1) exhibit not only potent hypoglycemic and lipid-lowering effects but also aldose reductase inhibitory activity, leading to the completion of the invention.

Namely, the invention provides N-substituted dioxothiazolidylbenzamide derivatives represented by the general formula (1)

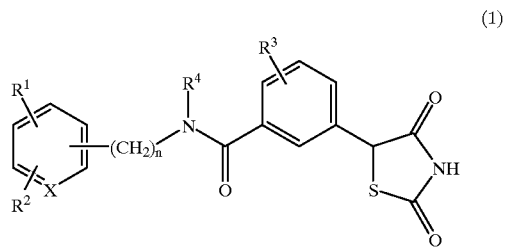

(1)

[wherein $R^1$ and $R^2$ denote identically or differently hydrogen atoms, lower alkyl groups with carbon atoms of 1 to 4, lower alkoxy groups with carbon atoms of 1 to 3, lower haloalkyl groups with carbon atoms of 1 to 3, lower haloalkoxy groups with carbon atoms of 1 to 3, halogen atoms or hydroxyl groups, or $R^1$ and $R^2$ combine to form a methylenedioxy group, $R^3$ denotes a hydrogen atom, lower alkoxy group with carbon atoms of 1 to 3, hydroxyl group or halogen atom, $R^4$ denotes a hydrogen atom or lower alkyl group with carbon atoms of 1 to 3, n denotes an integer of 0 to 2, and X denotes N or CH], and their pharmacologically acceptable salts.

The salts of the compounds represented by the general formula (1) in the invention are of common use, and metal salts, for example, pharmacologically acceptable salts such as alkali metal salts (e.g. sodium salt, potassium salt, etc.), alkaline earth metal salts (e.g. calcium salt, magnesium salt, etc.) and aluminum salt can be mentioned.

Moreover, the compounds represented by the general formula (1) in the invention sometimes includes optical isomers based on the portion of thiazolidine, but such isomers and their mixtures are all to be included in the scope of this invention.

Furthermore, for the compounds represented by the general formula (1), existence of various tautomers is conceivable. For example, they are as shown below.

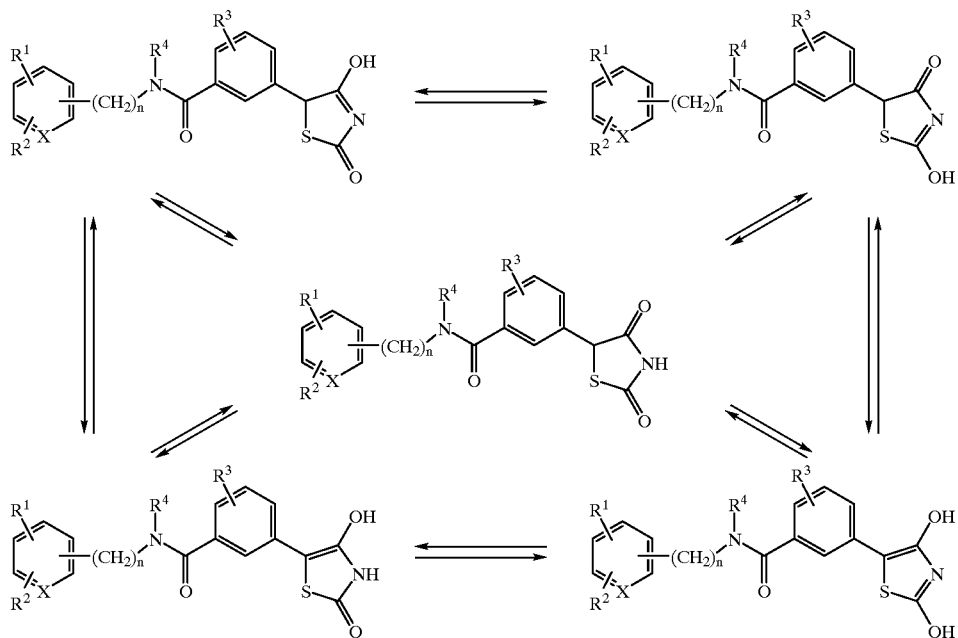

[wherein $R^1$, $R^2$, $R^3$, and $R^4$ n and X are as described above].

In the general formula (1), these isomers and their mixtures are all to be included in the scope of this invention.

In the general formula (1) of the invention, for the "lower alkyl group", straight chain or branched one with carbon atoms 1 to 4 such as methyl, ethyl, propyl and butyl is mentioned.

For the "lower alkoxy group", straight chain or branched ones with carbon atoms of 1 to 3 such as methoxy, ethoxy and propoxy are mentioned.

For the "lower haloalkyl group", straight chain or branched one with carbon atoms of 1 to 3 such as trifluoromethyl are mentioned.

For the "lower haloalkoxy group", straight chain or branched ones with carbon atoms of 1 to 3 such as trifluoromethoxy are mentioned.

For the "halogen atom", fluorine atom, chlorine atom, bromine atom and iodine atom are mentioned.

According to the invention, the compounds of the general formula (1) can be prepared through following process.

Compounds of the general formula (1) can be prepared by reacting compounds of the general formula (5) with compounds of the general formula (6).

(1)

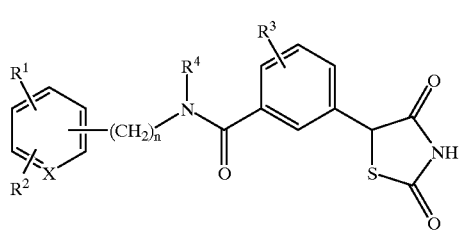

[wherein $R^1$ and $R^2$ denote identically or differently hydrogen atoms, lower alkyl groups with carbon atoms of 1 to 4, lower alkoxy groups with carbon atoms of 1 to 3, lower haloalkyl groups with carbon atoms of 1 to 3, lower haloalkoxy groups with carbon atoms of 1 to 3, halogen atoms or hydroxyl groups, or $R^1$ and $R^2$ combine to form a methylenedioxy group, $R^3$ denotes a hydrogen atom, lower alkoxy group with carbon atoms of 1 to 3, hydroxyl group or halogen atom, $R^4$ denotes a hydrogen or lower alkyl group with carbon atoms of 1 to 3, n denotes an integer of 0 to 2, and X denotes N or CH].

(5)

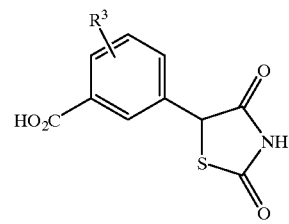

[wherein $R^3$ is as described above].

(6)

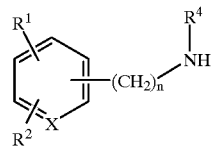

[wherein $R^1$, $R^2$, $R^4$, n and X are as described above].

The reaction can be conducted by treating with condensing agent, for example, 1-ethyl-3-(3'-dimethylaminopropyl) carbodiimide, diethyl cyanophosphate or the like in an organic solvent, for example, dimethyl sulfoxide, N,N-dimethylformamide or the like. Moreover, if necessary, an organic base, for example, triethylamine or the like may be added.

As the reaction temperature, ice cooling to room temperature can be used.

Compounds of the general formula (5) can be prepared by reacting compounds of following general formula (4) with thiourea followed by hydrolysis.

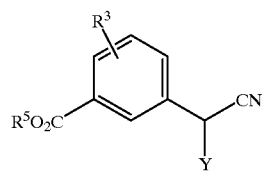
(4)

[wherein $R^3$ is as described above, $R^5$ denotes a lower alkyl group with carbon atoms of 1 to 3, and Y denotes a halogen atom].

The reaction between the general formula (4) and thiourea can be conducted at room temperature to solvent-refluxing temperature in an organic solvent, for example, in alcohol such as ethanol, but solvent-refluxing temperature is preferable. If necessary, a base (sodium acetate or the like) may be added. Successive hydrolysis reaction can be conducted at room temperature to solvent-refluxing temperature, preferably at solvent-refluxing temperature, under acidic condition, for example, in hydrochloric acid or mixed solvent of hydrochloric acid with organic solvent (ethanol or the like). Further, if necessary, it may be conducted at room temperature to solvent-refluxing temperature under basic condition, for example, in an aqueous solution of sodium hydroxide or a mixed solvent of aqueous solution of sodium hydroxide with organic solvent (ethanol or the like).

Compounds of the general formula (4) can be prepared by halogenating the compounds of general formula (3).

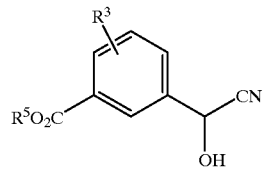
(3)

[wherein $R^3$ and $R^5$ are as described above].

The reaction can be conducted by treating with halogenating agent, for example, thionyl chloride, thionyl bromide or the like in an organic solvent, for example, chloroform, methylene chloride or the like, or without solvent. Moreover, if necessary, N,N-dimethylformamide may be added. As the reaction temperature, room temperature to solvent-refluxing temperature can be used.

Compounds of general formula (3) can be prepared by reacting the compounds of general formula (2) with cyanide.

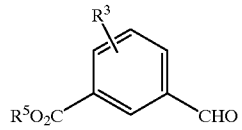
(2)

[wherein $R^3$ and $R^5$ are as described above].

The reaction can be conducted by reacting with trimethylsilyl cyanide at ice cooling to room temperature in an organic solvent, for example, chloroform, methylene chloride or the like in the presence of catalytic amount of Lewis acid, for example, zinc iodide, and then treating at cooling with ice to room temperature under acidic condition, for example, in hydrochloric acid or mixed solvent of hydrochloric acid with organic solvent (1,3-dioxirane or the like). Also, they can be prepared by converting the compounds of general formula (2) to bisulfite adduct, and then reacting with cyanide (potassium cyanide or the like) in a two-phase system, that is, water-organic solvent system.

Best embodiment to put the invention to practice

Next, the invention will be illustrated based on concrete examples, but the invention is not confined to these examples. The abbreviations used in the examples have following meanings.

MS Mass spectrum

DMF N,N-dimethylformamide

IPE Diisopropyl ether

EXAMPLE 1

Methyl 5-(1-cyano-1-hydroxymethyl)-2-methoxybenzoate

To a solution of methyl 5-formyl-2-methoxybenzoate (55.61 g) and zinc iodide (960 mg) in methylene chloride (560 ml) was added trimethylsilyl cyanide (48 ml) in an argon atmosphere under ice cooling and stirring, and the mixture was stirred for 6.5 hours as it was. The reaction mixture was poured into water and methylene chloride layer was separated. After washing with water, it was dried over anhydrous sodium sulfate and concentrated under reduced pressure. The residue was dissolved into 1,3-dioxolane (400 ml) and 2 N hydrochloric acid (200 ml) was added, which was allowed to stand for 1.5 hours at room temperature. The reaction liquor was poured into water and extracted with ethyl acetate. This was washed with water, brine and then dried over anhydrous sodium sulfate. This was concentrated to about 200 ml under reduced pressure and the crystals deposited were collected by filtration and dried to obtain 39.41 g (62%) of aimed compound as pale yellow crystals.

Melting point: 145.0~148.0° C.

MS (m/z):221 (M$^+$)

EXAMPLES 2 through 5

Similarly to Example 1, compounds in Table 1 were obtained.

TABLE 1

| Example | $R^3$ | $R^5$ | M. P. (° C.) | MS (m/z): M$^+$ |
|---|---|---|---|---|
| 2 | EtO | Et | 72.0~77.0 | — |
| 3 | i-Pro | Me | Oily product | — |
| 4 | F | Me | 85.0~86.0 | 209 |
| 5 | H | Me | Oily product | 191 |

EXAMPLE 6

Methyl 5-(1-chloro-1-cyanomethyl)-2-methoxybenzoate

To a suspension of methyl 5-(1-cyano-1-hydroxymethyl)-2-methoxybenzoate (2.15 g) in chloroform (40 ml) were added thionyl chloride (2.0 ml) and DMF (2 drops), and the mixture was refluxed for 30 minutes under heat. After cooling, the reaction mixture was washed with water, aqueous solution of sodium hydrogencarbonate and saturated brine in sequence and dried over anhydrous sodium sulfate.

This was concentrated under reduced pressure to obtain 2.37 g of aimed compound as an oily product.

MS (m/z):239,241 (M+)

EXAMPLES 7 through 10

Similarly to Example 6, compounds in Table 2 were obtained.

TABLE 2

| Example | $R^3$ | $R^5$ | Property | MS (m/z): M+ |
|---------|-------|-------|----------|--------------|
| 7 | EtO | Et | Oily product | — |
| 8 | i-Pro | Me | Oily product | — |
| 9 | F | Me | Oily product | 227, 229 |
| 10 | H | Me | Oily product | 209, 211 |

EXAMPLE 11

5-(2,4-Dioxothiazolidin-5-yl)-2-methoxybenzoic acid

To a solution of methyl 5-(1-chloro-1-cyanomethyl)-2-methoxybenzoate (2.37 g) in ethanol (30 ml) was added thiourea (910 mg), and the mixture was refluxed for 3 hours. After cooling, 3 N hydrochloric acid (30 ml) was added, which was refluxed for 16 hours. After cooling, the reaction mixture was poured into water, which was extracted with ethyl acetate. After washing with water, the extract was dried over anhydrous sodium sulfate.

The extract was concentrated under reduced pressure and the residue was dissolved into methanol (50 ml). Then, aqueous solution of sodium hydroxide (sodium hydroxide: 2.50 g, water: 15 ml was added and the mixture was stirred for 1 hour at 60° C. After cooling, water was added to the reaction mixture, which was washed with ethyl acetate. After acidified with 2 N hydrochloric acid, this was extracted with ethyl acetate and, after washing with water, dried over anhydrous sodium sulfate. Solids obtained by concentrating under reduced pressure were recrystallized from methylene chloride-hexane to obtain 1.10 g (42%) of aimed compound as pale yellow crystals. Melting point: 168.5~169.5° C. MS (m/z): 267 (M+)

EXAMPLES 12 through 15

Similarly to Example 11, compounds in Table 3 were obtained.

TABLE 3

| Example | $R^3$ | M. P. (° C.) | MS (m/z): M+ |
|---------|-------|--------------|--------------|
| 12 | EtO | 155.0~160.0 | — |
| 13 | i-Pro | Amorphous | 295 |
| 14 | F | Amorphous | 255 |
| 15 | H | 245.0~247.0 | 237 |

EXAMPLE 16

N-(4-trifluoromethylbenzyl)-5-(2,4-dioxothiazolidin-5-yl)-2-methoxybenzamide

To a solution of 4-trifluoromethylbenzylamine (71.9 g) in DMF (1 L) were added 5-(2,4-dioxothiazolidin-5-yl)-2-methoxybenzoic acid (98.7 g), diethyl cyanophosphate (94.7 g) and triethylamine (63 ml) under cooling with ice and stirring, and the mixture was stirred for 15 minutes as it was. Thereafter, it was stirred for 7 hours at room temperature. The reaction mixture was poured into water, which was extracted with ethyl acetate and, after washing with water, dried over anhydrous sodium sulfate. This was concentrated under reduced pressure and the residue was dissolved into ethanol. After treating with activated charcoal, this was filtered through celite and water was added to the filtrate. The crystals deposited were collected by filtration and dried to obtain 83.6 g (53%) of aimed compound as colorless powder. Melting point: 168.0~169.0° C.

Elemental analysis (%): For $C_{19}H_{15}F_3 N_2 O_4 S$ C H N

Calculated: 53.77 3.56 6.60

Found: 53.92 3.69 6.81

EXAMPLES 17 through 33

Similarly to Example 16, compounds in Table 4 and Table 5 were obtained.

TABLE 4

[Structure: substituted benzyl/phenethyl group with R¹, R² on ring, (CH₂)ₙ linker, N(R⁴)-C(=O) amide, to benzene with R³ substituent, bearing thiazolidine-2,4-dione]

| Example | R¹, R² | R³ | R⁴ | n | M.P. (°C) (Recryst. solvent) | Composition formula | C Calcd./Found | H | N |
|---|---|---|---|---|---|---|---|---|---|
| 17 | 3-$CF_3$ | MeO | H | 1 | 165.0~167.0 (methylene chloride) | $C_{19}H_{15}F_3N_2O_4S$ | 53.77 / 53.80 | 3.56 / 3.52 | 6.60 / 6.61 |
| 18 | 2-$CF_3$ | MeO | H | 1 | 107.0~110.0 (metylene chloride-acetone) | $C_{19}H_{15}F_3N_2O_4S$ | 53.77 / 53.70 | 3.56 / 3.43 | 6.60 / 6.64 |
| 19 | H | MeO | H | 1 | 220.0~222.0 (ethyl acetate-acetone) | $C_{18}H_{16}N_2O_4S$ | 60.66 / 60.74 | 4.52 / 4.53 | 7.86 / 7.75 |
| 20 | 4-t-Bu | MeO | H | 1 | 186.0~187.0 (methylene chloride-hexane) | $C_{22}H_{24}N_2O_4S$ | 64.06 / 63.99 | 5.86 / 6.03 | 6.79 / 6.77 |
| 21 | 3,4-methylenedioxy | MeO | H | 1 | 185.0~187.0 (methylene chloride-acetone) | $C_{19}H_{16}N_2O_6S \cdot \frac{1}{2}H_2O$ | 55.74 / 55.78 | 4.19 / 3.81 | 6.84 / 6.75 |
| 22 | 4-$CF_3O$ | MeO | H | 1 | 159.0~161.0 (ethyl acetate) | $C_{19}H_{15}F_3N_2O_5S$ | 51.82 / 51.64 | 3.43 / 3.42 | 6.36 / 6.66 |
| 23 | 3,5-$CF_3$ | MeO | H | 1 | 193.0~195.0 (methylene chloride) | $C_{20}H_{14}F_6N_2O_4S$ | 48.79 / 48.91 | 2.87 / 2.86 | 5.69 / 5.92 |
| 24 | 4-$CF_3$ | MeO | H | 0 | 203.0~205.0 (ethyl acetate-hexane) | $C_{13}H_{13}F_3N_2O_4S$ | 52.68 / 52.68 | 3.19 / 3.22 | 6.83 / 7.08 |
| 25 | 4-$CF_3$ | MeO | H | 2 | 96.0~99.0 (methylene chloride-hexane) | $C_{20}H_{17}F_3N_2O_4S \cdot \frac{1}{10}H_2O$ | 54.57 / 54.48 | 3.94 / 3.82 | 6.36 / 6.35 |
| 26 | 4-$CF_3$ | EtO | H | 1 | 85.0~88.0 (ethanol) | $C_{20}H_{17}F_3N_2O_4S$ | 54.79 / 54.82 | 3.91 / 3.81 | 6.39 / 6.29 |
| 27 | 4-$CF_3$ | i-Pro | H | 1 | 193.0~194.0 (methylene chloride-hexane) | $C_{21}H_{19}F_3N_2O_4S$ | 55.75 / 55.74 | 4.23 / 4.21 | 6.19 / 6.36 |
| 28 | 3,4-methylenedioxy | EtO | H | 1 | 164.0~166.0 (ethanol) | $C_{20}H_{18}N_2O_6S$ | 57.96 / 57.91 | 4.38 / 4.41 | 6.76 / 6.70 |
| 29 | 4-$CF_3$ | F | H | 1 | 158.0~159.0 (methylene chloride-hexane) | $C_{18}H_{12}F_4N_2O_4S$ | 52.43 / 52.36 | 2.93 / 2.85 | 6.79 / 6.73 |
| 30 | 4-$CF_3$ | H | H | 1 | 165.5~168.0 (ethanol) | $C_{18}H_{13}F_3N_2O_4S$ | 54.82 / 54.85 | 3.32 / 3.43 | 7.10 / 7.01 |
| 31 | 4-$CF_3$ | MeO | Me | 1 | 150.0~151.5 (ether-IPE) | $C_{20}H_{17}F_3N_2O_4S$ | 54.79 / 54.79 | 3.91 / 4.20 | 6.39 / 6.34 |

TABLE 5

[Structure: pyridine-CH₂-NH-C(=O)- attached to MeO-substituted benzene bearing thiazolidine-2,4-dione]

| Example | Bonding position of pyridine ring | M. P. (°C) (Recryst. solvent) | Composition formula | C Calcd./Found | H | N |
|---|---|---|---|---|---|---|
| 32 | 3-position | 206.0~208.0 (DMF-methanol) | $C_{17}H_{15}N_3O_4S$ | 57.13 / 56.97 | 4.23 / 4.21 | 11.76 / 11.75 |
| 33 | 2-position | 238.0~239.0 (DMF-methanol) | $C_{17}H_{15}N_3O_4S$ | 57.13 / 56.83 | 4.23 / 4.46 | 11.76 / 11.80 |

Test Example 1

Employing inherited obese mice (C57BL ob/ob), prior to test, the blood sugar level was determined by collecting blood from caudal vein. The mice were grouped so as not to cause any difference in the blood sugar level, and the compounds of Example 16, 17 and 29 were administered orally for 5 days at a dosage of 10 mg/kg. For the glucose tolerance test, 2 g/kg of glucose were administered orally after fasting overnight and the blood sugar levels at 0 minute, 30 minutes and 60 minutes were determined. The blood sugar-lowering rate was calculated from following formula.

Blood sugar-lowering rate (%) =

$$\frac{[(\text{Sum of blood sugar levels of vehicle control group at } 0, 30 \text{ and } 60 \text{ min after glucose dosing}) - (\text{Sum of blood sugar levels of each at } 0, 30 \text{ and } 60 \text{ min after glucose dosing})]}{(\text{Sum of blood sugar levels of vehicle control group at } 0, 30 \text{ and } 60 \text{ min after glucose dosing})} \times 100$$

Results are shown in Table 6. From these results, it was shown that the inventive compounds had potent hypoglycemic effects.

TABLE 6

| Compound | Dosage (mg/kg) | Blood sugar-depressing rate (%) |
|---|---|---|
| Example 16 | 10 | 48 |
| Example 17 | 10 | 42 |
| Example 29 | 10 | 30 |

Test Example 2

Against aldose reductase extracted from rat lens, the in-vitro inhibitory effect of the compound of Example 16 was investigated by the method of Hayman and Kinoshita (Journal of Biological Chemistry, vol. 240, p. 877 (1965)).

Result is shown in Table 7. From this result, it was shown that the inventive compound had potent inhibitory effect on aldose reductase activity.

TABLE 7

| Compound | IC$_{50}$ value |
|---|---|
| Example 16 | 2.3 × 10$^{-8}$ M |

Text Example 3

Employing inherited obese mice (C57BL ob/ob), the compound of Example 16 was administered orally for 2 weeks at following dosages, and thereafter the triglyceride level in blood was determined. The triglyceride-lowering rate in blood was calculated from following formula.

$$\frac{[(\text{Measured level of vehicle control group}) - (\text{Measured level of each dosing group})]}{(\text{Measured level of vehicle control group})} \times 100$$

Results are shown in Table 8. From these results, it was shown that the inventive compound has potent lipid-lowering effect.

TABLE 8

| Compound | Dosage (mg/kg) | In-blood triglyceride depressing rate (%) |
|---|---|---|
| Example 16 | 3 | 51 |
|  | 10 | 70 |

We claim:

1. An N-substituted dioxothiazolidylbenzamide compound having the formula (I):

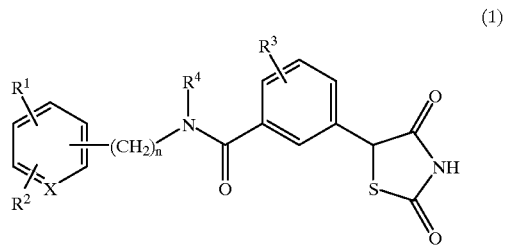

(1)

wherein $R^1$ and $R^2$ are each independently hydrogen, $C_1$–$C_4$ lower alkyl, $C_1$–$C_3$ lower alkoxy, $C_1$–$C_3$ haloalkyl, $C_1$–$C_3$ haloalkoxy, halogen or hydroxyl; or $R^1$ or $R^2$ together form methylenedioxy; $R^3$ is hydrogen, $C_1$–$C_3$ lower alkoxy, hydroxy or halogen; $R^4$ is hydrogen or $C_1$–$C_3$ alkyl; n is an integer of 0 to 2; and X is CH; or a pharmaceutically acceptable salt thereof.

2. The N-substituted dioxothiazolidylbenzamide compound of claim 1, wherein $R^1$ and $R^2$ are each independently 3-CF$_3$, H, 4-t-bu, 4-CF$_3$O, or 4-CF$_3$ or together form 3,4-methylenedioxy.

3. The N-substituted dioxothiazolidylbenzamide compound of claim 1, wherein $R^4$ is H or CH$_3$.

4. The N-substituted dioxothiazolidylbenzamide compound of claim 1, wherein n is 1.

5. The N-substituted dioxothiazolidylbenzamide compound of claim 1, which is N-(4-trifluromethylbenzyl)-5-(2,4,-dioxothiazolidine-5-yl)-2-methoxybenzamide, or a pharmaceutically acceptable salt thereof.

6. The N-substituted dioxothiazolidylbenzamide compound of claim 1, which is N-(3-trifluoromethylbenzyl)-5-(2,4-dioxothiazolidin-5-yl)-2-methoxybenzamide, or a pharmaceutically acceptable salt thereof.

7. The N-substituted dioxothiazolidylbenzamide compound of claim 1, wherein said pharmaceutically acceptable salt is selected from the group consisting of alkali metal salts, alkaline earth metal salts and aluminum salt.

8. The N-substituted dioxothiazolidylbenzamide compound of claim 4, wherein said alkali metal salts are selected from the group consisting of sodium and potassium salts.

9. The N-substituted dioxothiazolidylbenzamide compound of claim 7, wherein said alkaline metal salts are selected from the group consisting of calcium and magnesium salts.

10. The N-substituted dioxothiazolidyl benzamide compound of claim 1, which is an optical isomer mixture.

11. The N-substituted dioxothiazolidyl benzamide compound of claim 10, which is an optical isomer.

12. A hypoglycemic composition, comprising:
a) one or more of the N-substituted dioxothiazolidylbenzamide compounds of claim 1; and
b) a pharmaceutically acceptable carrier.

* * * * *